United States Patent [19]
Monnier et al.

[11] Patent Number: 4,897,498
[45] Date of Patent: Jan. 30, 1990

[54] SELECTIVE MONOEPOXIDATION OF OLEFINS

[75] Inventors: John R. Monnier, Fairport; Peter J. Muehlbauer, Spencerport, both of N.Y.

[73] Assignee: Eastman Kodak Company, Rochester, N.Y.

[21] Appl. No.: 149,297

[22] Filed: Jan. 28, 1988

[51] Int. Cl.$^4$ .......................................... C07D 301/10
[52] U.S. Cl. .................................. 549/534; 549/536; 549/537; 549/462; 502/347
[58] Field of Search ............... 549/534, 536, 537, 462; 502/347

[56] References Cited

U.S. PATENT DOCUMENTS

| | | | |
|---|---|---|---|
| 2,040,782 | 5/1936 | Van Peski | 260/54 |
| 2,279,470 | 4/1942 | Law et al. | 549/534 |
| 2,404,438 | 7/1946 | Evans | 549/534 |
| 2,421,862 | 6/1947 | Arundale et al. | 260/635 |
| 2,709,173 | 5/1955 | Brengle et al. | 260/348.5 |
| 3,538,124 | 11/1970 | Sheng et al. | 260/348.5 |
| 3,560,530 | 2/1971 | Stiles | 260/348.5 |
| 3,699,133 | 10/1972 | Messina et al. | 260/348.5 |
| 3,701,719 | 10/1972 | Leduc et al. | 204/131 |
| 3,702,855 | 11/1972 | Bell et al. | 260/348.5 |
| 3,716,562 | 2/1973 | Pregaglia et al. | 260/348.5 |
| 3,725,307 | 4/1973 | Brown et al. | 549/534 |
| 4,026,908 | 5/1977 | Pralus et al. | 260/348.5 |
| 4,064,146 | 12/1977 | Neri et al. | 260/348.16 |
| 4,168,247 | 9/1979 | Hayden et al. | 252/476 |
| 4,215,059 | 7/1980 | Gipson | 260/348.29 |
| 4,215,060 | 7/1980 | Gipson | 260/348.29 |
| 4,226,782 | 10/1980 | Hayden et al. | 260/348.34 |
| 4,241,184 | 12/1980 | Hou et al. | 435/148 |
| 4,247,641 | 1/1981 | Neidleman et al. | 435/123 |
| 4,269,940 | 5/1981 | Patel et al. | 435/148 |
| 4,277,405 | 7/1981 | Apanel | 260/348.21 |
| 4,284,723 | 8/1981 | Neidleman et al. | 435/123 |
| 4,293,444 | 10/1981 | Parthasarathy et al. | 252/432 |
| 4,347,319 | 8/1982 | Hou et al. | 435/123 |
| 4,376,865 | 3/1983 | Apanel | 549/521 |
| 4,390,738 | 6/1983 | Waddan et al. | 568/857 |
| 4,429,055 | 1/1984 | Rao | 502/202 |
| 4,474,997 | 10/1984 | Rao | 568/473 |
| 4,483,994 | 11/1984 | Jacobson | 549/230 |
| 4,571,290 | 2/1986 | Ward et al. | 204/157.69 |
| 4,575,494 | 3/1986 | Young, Jr. et al. | 502/243 |
| 4,645,754 | 2/1987 | Tamura et al. | 502/527 |
| 4,774,222 | 9/1988 | Rashkin | 502/347 |

FOREIGN PATENT DOCUMENTS

| | | |
|---|---|---|
| 0003642 | 8/1979 | European Pat. Off. . |
| 0026827 | 8/1980 | European Pat. Off. . |
| 172565 | 2/1986 | European Pat. Off. . |
| 2523971 | 9/1983 | France . |
| 1327497 | 8/1973 | United Kingdom . |
| 1600747 | 10/1981 | United Kingdom . |

OTHER PUBLICATIONS

Chemical Abstracts, vol. 105, No. 24, Dec. 15, 1986, Columbus, Ohio, U.S.A.; Garfunkel, E.; Ding, X.; Dong, G.; Yang, S.; Hou, X.; Wang, X., "The effect of sodium edlayers on the absorption of oxygen on silver (100)", p. 347, col. 1, Abstract No. 214368m.
Chin. Phys. Lett. 1985, 2(9), 397–400.
Chemical Abstracts, vol. 102, No. 15, Apr. 15, 1985, Columbus, Ohio, U.S.A.; Campbell, Ch. T.; Paffett, M. T., "The role of chlorine promoters in catalytic ethylene epoxidation over the silver (110) surface", p. 572, col. 1, Abstract No. 131377a.
Appl. Surf. Sci. 1984, 19(1-4), 28–42.
Chemical and Engineering News, p. 24, Feb. 9, 1987.
Chemical and Engineering News, pp. 18–21, Aug. 31, 1987.
Industrial and Engineering Chemistry, vol. 44, No. 3, pp. 594–603, Mar. 1952.
Bulletin of the Chemical Society of Japan, vol. 48 (No. 12) pp. 3518–3522 (1975).
Bulletin of the Chemical Society of Japan, vol. 51 (No. 10) pp. 3061–3062 (1978).
Akimoto & Echigoya in J. Chemical Society, Faraday Trans. 1, vol. 75, pp. 1757–1768, 1979.
Industrial Engineering Chemistry Production Research Developments, 1983, vol. 22, pp. 570–577.
Journal of Molecular Catalysis, vol. 35, pp. 255–265 (1986).
Journal of Organic Chemistry, vol. 41, No. 8, Apr. 16, 1976, R. A. Budnik et al.: "Epoxidation of Olefins with Molecular Osygen in the Presence of Cobalt Complexes", pp. 1384–1389.
Benson, S., "Journal of Am. Chem. Soc.", 87(5), pp. 972–979, 1965.

Primary Examiner—Glennon H. Hollrah
Assistant Examiner—Ba K. Trinh
Attorney, Agent, or Firm—S. E. Reiter; William P. Heath, Jr.

[57] ABSTRACT

Process is disclosed for the selective mono epoxidation of olefins having no allylic hydrogens. Such olefins are contacted with an oxygen-containing gas in the presence of a silver catalyst under defined reaction conditions, thereby selectively producing monoepoxides in good yield.

14 Claims, No Drawings

SELECTIVE MONOEPOXIDATION OF OLEFINS

This invention relates to oxidation reactions. In one aspect, this invention relates to selective oxidation reactions for the production of epoxides from olefins.

BACKGROUND OF THE INVENTION

Epoxides are highly reactive chemical compounds which, as a result of their reactivity, can be used in a wide variety of applications. Unfortunately, due to the reactivity of epoxides, they are often difficult to prepare with high selectivity and in high yields. Ethylene is the only olefin which has been successfully oxidized employing molecular oxygen on a commercial scale to produce an epoxide.

Preferred catalysts employed for the oxidation of ethylene to produce ethylene oxide comprise silver on solid supports. When such catalysts are employed for the oxidation of olefins having longer chain lengths than ethylene, no epoxides are obtained, but instead various higher oxidation products (up to and including carbon dioxide and water) are obtained.

Alternate routes to epoxides other than ethylene oxide include the non-catalytic oxidation of olefins with peroxides. Such processes are not only uneconomical, but are also hazardous due to the large quantities of peroxide required for the desired conversion.

It would, therefore, be desirable to be able to catalytically oxidize olefins having longer chain lengths than ethylene to produce epoxides directly. Such processes would provide large quantities of highly reactive olefin derivatives which would find a wide range of uses, such as for example, as polymer cross-linking agents, as reactive chemical intermediates, as precursors for the production of organic solvents, and the like.

OBJECTS OF THE INVENTION

An object of the present invention, therefore, is to provide a catalytic process for the selective oxidation of olefins having a longer chain length than ethylene to selectively produce epoxides in high yield.

This and other objects of the present invention will become apparent from inspection of the detailed description and appended claims which follow.

STATEMENT OF THE INVENTION

In accordance with the present invention, we have discovered that olefins having no allylic hydrogens can be catalytically oxidized to produce a high selectivity of epoxide derivatives thereof by contacting the olefin feed with an oxygen-containing gas in the presence of a silver catalyst under defined oxidation conditions. The practice of the present invention makes possible the large scale production of such highly functionalized compounds as butadiene oxide, t-butyl ethylene oxide, vinyl furan oxide, and methyl epoxy vinyl ketone, employing readily available feedstocks (e.g., butadiene, t-butylethylene, vinyl furan, and methyl vinyl ketone, respectively). The only other material consumed during the invention reaction, besides the olefin feedstock, is molecular oxygen. Thus, the invention process is not only economical, but, since the reaction can be run in the continuous mode, it also makes possible the ready preparation of large quantities of these useful chemical compounds.

DETAILED DESCRIPTION OF THE INVENTION

In accordance with the present invention, we have developed a process for the selective mono-epoxidation of olefins having defined structure which comprises contacting the feed olefin with a sufficient quantity of an oxygen-containing gas so as to maintain the molar ratio of olefin to oxygen in the range of 0.01 up to 20, in the presence of a silver catalyst at a reaction pressure in the range of 0.1 up to 100 atmospheres and a temperature in the range of about 75° up to 325° C. for a reaction time sufficient to obtain olefin conversions in the range of about 0.5 up to 75 mole percent.

Olefins contemplated for use in the practice of the present invention are those which satisfy the following structural formula:

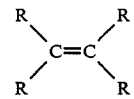

wherein each R is independently selected from the group consisting of:

(a) hydrogen, (b) aryl and substituted aryl groups having in the range of 7 up to 20 carbon atoms, (c) tertiary alkyl groups of the formula:

where each R' is independently:
R'',

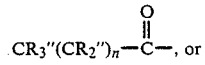

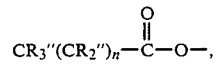

where R'' is H, $C_1$–$C_{10}$ alkyl or substituted alkyl, an aryl or substituted aryl group having 6 up to 20 carbon atoms, and n is a whole number from 0–12;

(d) $CR_3''$—$(CR_2'')_x$—O—, where x is a whole number from 1–12;

(e)

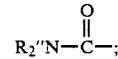

(f) $R_2''N$—; Lp (g) R''S—;

(h) $CR_2''=CR''+(CR''=CR'')_y$, where y is an integer from 0–20; and (i)

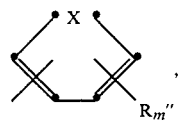

where X is O, S or NR''; and m is an integer from 0–3, with the proviso that said olefin have no allylic hydrogens and that at least one R-group not be hydrogen.

Exemplary olefins which satisfy the above structural formula include butadiene, divinyl benzene, tertiary butylethylene, vinyl furan, methyl vinyl ketone, N-vinyl pyrrolidone, and the like. A presently preferred olefin for use in the practice of the present invention is butadiene because of its ready availability, relatively low cost, and the wide range of possible uses for the epoxide reaction product.

The silver catalyst required for the practice of the present invention can be employed in either supported or unsupported forms.

When a support is employed, the loading level of silver on support typically falls within the range of about 0.5 up to 50 weight percent, calculated as elemental silver and based on the total weight of finished catalyst. Preferably, the loading level of silver on support falls within the range of about 1 up to 30 weight percent elemental silver; with loading levels in the range of about 2 up to 20 weight percent being most preferred.

It is presently preferred to apply the silver to a solid support for efficient use of the expensive silver component. Typical catalyst supports include
    silica,
    alumina,
    silica-alumina,
    zeolites,
    titanium oxide,
    lanthanum oxide,
    magnesium oxide,
    boron nitride,
    boron carbide,
    silicon nitride,
    silicon carbide,
    zinc oxide,
    tin oxide,
    iron oxide,
    calcium oxide,
    barium oxide,
    strontium oxide,
    zirconium oxide,
    carbon,
    boron phosphate,
    zirconium phosphate,
and the like, as well as mixtures of any two or more thereof.

Typically, these solid supports will have a surface area of less than about 50 m$^2$/g. Preferred supports will have a surface area of less than about 10 m$^2$/g and will be neutral or moderately basic in character. The presently most preferred supports have surface areas of less than about 1 m$^2$/g, and include alumina, silica, and silicon carbide.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid-solid contacting, catalyst durability, and the like make the use of defined shapes such as spheres, pellets, extrudates, rings, saddles, and the like preferred.

Especially preferred supports are those which have been treated with in the range of 0.001 up to 10 weight %, based on the total weight of catalyst, including support, of at least one promoter selected from the group consisting of:
    the salts of alkali metals,
    the oxides of alkali metals,
    the salts of alkaline earth metals,
    the oxides of alkaline earth metals,
    organic halides,
    inorganic halides,
    acid halides, and
    elemental halogens.

Exemplary salts of alkali metals include sodium nitrate, sodium sulfate, sodium chloride, sodium bromide, rubidium nitrate, rubidium acetate, lithium sulfate, lithium chloride, cesium nitrate, cesium chloride, cesium bromide, and the like; exemplary oxides of alkali metals include sodium oxide, sodium hydroxide, cesium oxide, cesium hydroxide, lithium oxide, lithium hydroxide, and the like; exemplary salts of alkaline earth metals include barium nitrate, barium acetate, calcium nitrate, calcium acetate, calcium chloride, and the like; exemplary oxides of alkaline earth metals include barium oxide, barium hydroxide, calcium oxide, calcium hydroxide, and the like; exemplary organic halides include carbon tetrachloride, carbon tetrabromide, chloroform, bromoform, methylene chloride, methylene bromide, ethylene dibromide, ethylene dichloride, vinyl chloride, chlorobenzene, bromobenzene, $\alpha$-chlorotoluene, 2-chlorotoluene, and the like; exemplary inorganic halides include HCl, HBr, and the like; exemplary acid halides include HOCl, HOBr and the like; and the elemental halogens include chloride, bromine and iodine. Those of skill in the art recognize that the above-recited compounds are merely illustrative of the compounds which are useful as promoters in the practice of the present invention, and that many other compounds which fall within the generic categories set forth above can also be identified and would be expected to also impart enhanced activity and/or selectivity to the catalyst employed in the practice of the present invention.

Of the above compounds, the alkali metal halides are most preferred. Exemplary preferred alkali metal halides include cesium chloride, rubidium chloride, potassium chloride, sodium chloride, sodium bromide, potassium bromide, rubidium bromide, cesium bromide, and the like.

Those of skill in the art recognize that catalysts employed in the practice of the present invention can include additional components which may modify catalyst activity and/or selectivity. Such additives may be incorporated into the finished catalyst because their presence aids catalyst preparation, e.g., binders, die lubricants, and the like; or additives may be incorporated as extenders to reduce the cost of catalyst preparation; or additives may be incorporated to extend the operating ranges for reaction temperature and/or pressure; or additives may be incorporated to increase catalyst lifetime under reaction conditions and/or to modify the amounts of catalyst promoters employed to produce enhanced catalyst activity. It is recognized, of course, that some additives (e.g., cesium) are suitably employed in very low levels (i.e., milligrams of additive per gram of catalyst); while other additives (i.e., binders, diluents, and the like) re suitably employed at significantly higher levels (i.e., as a significant percentage of the total catalyst weight).

Supported catalysts can be prepared employing techniques well known to those of skill in the art, such as, for example, by precipitation of the active metals on the support, by impregnation, by coprecipitation of support and active metals, by grinding together solid support and active metal(s) in particulate form; and the like. When a promoter is also present in the catalyst, the order in which it is incorporated into the catalyst is not critical, i.e., support can be contacted with a silver source, then promoter; or support can be contacted with promoter, then a silver source; or support can be contacted simultaneously with both promoter and a silver source; and other such variations.

Most any source of silver is suitable for use in preparing the catalyst employed in the practice of the present invention. Since a preferred method for preparation of supported catalyst involves impregnation of support with a solution of a silver compound, soluble silver compounds are a presently preferred source of silver. Exemplary compounds are silver nitrate, slver oxalate, silver acetate, and the like. Those of skill in the art recognize that certain organic silver compounds require the addition of ammonia or an amine in order to solubilize the organic silver compound in aqueous medium; thus, the use of such solvation-promoting additives is contemplated in the practice of the present invention.

The process of the present invention is carried out under oxidation conditions, i.e., in the presence of sufficient quantities of an oxygen-containing gas to provide a molar ratio of olefin to oxygen in the range of about 0.01 up to 20. While greater or lesser quantities of molecular oxygen can be employed, sufficient quantities of oxygen should be provided to insure that undesirably low levels of olefin conversion do not occur, while excessively high oxygen concentrations should be avoided to prevent the formation of explosive mixtures.

Suitable oxygen-containing gases include air, oxygen-enriched air, substantially purified oxygen, oxygen diluted with inert gases such as $N_2$, Ar, $CO_2$ or $CH_4$, and the like.

Suitable reaction temperatures fall within the range of about 75° up to 325° C. At lower temperatures, the reaction proceeds so slowly as to be impractical, while at higher temperatures undesirable levels of by-products, e.g., carbon dioxide, are obtained. Preferred reaction temperatures fall within the range of about 125° up to 275° C.; with temperatures in the range of about 175° up to 250° C. being most preferred because selectivity to the desired monoepoxide falls off at temperatures significantly above 250° C. and space-time yields are undesirably low at temperatures below about 175° C.

The reaction pressure can vary within wide ranges, with typical limits of about 0.1 up to 100 atmospheres being chosen primarily as a function of safety, handling, equipment and other practical considerations. Preferably, reaction pressure is maintained in the range of about 1 up to 30 atmospheres.

Reaction times suitable for the practice of the present invention can vary within wide ranges. Generally, olefin, oxygen and catalyst are maintained in contact for a time sufficient to obtain olefin conversions in the range of about 0.5 up to 75 mole percent. Reaction times sufficient to obtain olefin conversion in the range of about 5 up to 30 mole percent are preferred for efficient utilization of the reactor capacity.

Those of skill in the art recognize that the actual contact times required to accomplish the desired conversion levels can vary within wide ranges, depending on such factors as vessel size, olefin to oxygen ratios, the silver loading level on the catalyst, the presence or absence of any catalyst modifiers (and their loading levels), the reaction temperature and pressure, and the like.

The invention process can be carried out in either batch or continuous mode. Continuous reaction is presently preferred since high reactor throughput and high purity product is obtained in this manner. The batch mode is satisfactorily employed when high volume of reactant throughput is not required, for example, for liquid phase reactions.

For continuous mode of reaction carried out in the gas phase, typical gas hourly space velocities (GHSV) fall within the range of about 100 up to 30,000 $hr^{-1}$. GHSV in the range of about 200 up to 20,000 $hr^{-1}$ are preferred, with GHSV in the range of about 300 up to 8000 $hr^{-1}$ being most preferred because under such conditions the most desirable combination of feed olefin conversion and product selectivities are obtained.

When continuous mode of reaction is carried out in the liquid phase, typical liquid hourly space velocities (LHSV) employed will give contact times analogous to that obtained at the GHSV values given above. Most preferably, LHSV employed will fall in a range so as to produce the most desirable combination of feed olefin conversion levels and high product selectivity.

Recovery of product produced in the practice of the present invention can readily be carried out employing techniques well known by those of skill in the art. For example, where reaction is carried out in the continuous mode, unreacted starting material is initially separated from reaction products; and the desired product then isolated from the resulting product mixture by distillation, crystallization, extraction, or the like. Since the selectivity to the desired epoxide product is generally quite high, there are only small amounts of undesired reaction products from which to isolate the desired product.

The invention will now be described in greater detail by reference to the following non-limiting examples.

EXAMPLE 1

Catalyst Preparation

Catalysts were typically prepared by impregnation of support with a solution of a silver compound (and optionally a promoter) in 1-2 volumes of solvent relative to the volume of support being treated. Thus, for example a 14.2% Ag (as determined by neutron activation analysis) on $Al_2O_3$ support was prepared by dissolving 202.3 grams of Kodak silver nitrate in 500 mL of distilled water. Five hundred grams of calcined $Al_2O_3$ 3/16" spheres (surface area 0.39 $m^2$/g, total pore volume 0.36 cc(Hg)/gm, median pore diameter 5.4$\mu$, packing density 0.94 $g/cm^3$, crush strength 65.2 pounds, chemical composition (wt %): $Al_2O_3$-86.1, $SiO_2$-11.8, $Fe_2O_3$-0.2, $TiO_2$-0.1, CaO-0.4, MgO-0.4, $Na_2O$-0.4, $K_2O$-0.6) were added to the silver-containing solution, the mixture tumbled for 30 minutes at 50° C., then water removed under vacuum at 60° C. The resulting pellets were then dried for 30 minutes at 120° C. in a force air oven. This material could be calcined and used directly for oxidation of olefin feed or treated with a promoter and then calcined.

Prior to catalyst evaluation (and either before or after further treatment with promoter), all catalysts were optionally calcined in an oxygen-containing atmosphere (air or oxygen-supplemented helium) at about 350° C. for about 4 hours. Following calcination, all catalysts were subjected to an activation treatment at a temperature in the range of about 300°-350° C. in an atmosphere initially containing about 2-5% hydrogen in an inert carrier such as helium or nitrogen. The hydrogen content of the activating atmosphere was gradually increased up to a final hydrogen concentration of about 20-25% at a controlled rate so that the activation temperature did not exceed 350° C. After the temperature was maintained for about 1 hour at a hydrogen concentration in the range of about 20-25%, catalyst was ready for use.

When the Ag/Al$_2$O$_3$ catalyst was treated with promoter, a quantity of catalyst was contacted with 1-2 volumes of aqueous promoter, then dried as previously described. In this way, the following catalysts were prepared (Unless otherwise noted in the Table, catalyst support employed was a fluidizable powder having a surface area of 0.26 m$^2$/g, a total pore volume of 0.675 cc (Hg)/gm, median pore diameter 19$\mu$, a packing density of 0.98 g/cm$^3$, and a chemical composition (wt %) as follows: Al$_2$O$_3$-84.7, SiO$_2$-13.4, Fe$_2$O$_3$-0.21, TiO$_2$-0.47, CaO-0.21, MgO-0.12, Na$_2$O-0.15, K$_2$O-0.26):

TABLE I

| Alumina-Supported Catalysts | | | |
|---|---|---|---|
| Catalyst | Silver loading, wt % (silver source) | Support | Promoter loading, mg/g* (Promoter Source) |
| A | 1.1 (AgNO$_3$) | Al$_2$O$_3$ | 0 |
| A' | 5.3 (AgNO$_3$) | Al$_2$O$_3$ | 0 |
| B | 15.2 (AgNO$_3$) | Al$_2$O$_3$ (pellets)[1] | 0 |
| B' | 15 (AgNO$_3$) | Al$_2$O$_3$ (spheres)[2] | 0 |
| B'' | 15 (AgNO$_3$) | Al$_2$O$_3$ (rings)[3] | 0 |
| C | 17 (AgNO$_3$) | Al$_2$O$_3$ | 0 |
| D | 19 (AgNO$_3$) | Al$_2$O$_3$ | 0 |
| E | 38 (AgNO$_3$) | Al$_2$O$_3$ | 0 |
| F | 5 (AgNO$_3$) | Al$_2$O$_3$ (spheres)[2] | 1.0 (CsCl) |
| G | 15 (AgNO$_3$) | Al$_2$O$_3$ (spheres)[4] | 1.0 (CsCl) |
| H | 15 (AgNO$_3$) | Al$_2$O$_3$ (spheres)[2] | 1.0 (CsCl) |
| I | 15 (AgNO$_3$) | Al$_2$O$_3$ (spheres)[2] | 1.25 (CsCl) |
| J | 15 (AgNO$_3$) | Al$_2$O$_3$ (spheres)[2] | 1.50 (CsCl) |
| K | 15 (AgNO$_3$) | Al$_2$O$_3$ (spheres)[2] | 1.0/0.024 (CsCl/Br$_2$)** |
| L | 15 (AgNO$_3$) | Al$_2$O$_3$ (spheres)[2] | 1.0/0.056 (CsCl/Br$_2$)** |
| M | 15 (AgNO$_3$) | Al$_2$O$_3$ (spheres)[2] | 1.0/0.12 (CsCl/Br$_2$)** |
| N | 15 (AgNO$_3$) | Al$_2$O$_3$ (spheres)[2] | 1.0/0.24 (CsCl/Br$_2$)** |
| O | 15 (AgNO$_3$) | Al$_2$O$_3$ (spheres)[2] | 1.0/0.24 (CsCl/Br$_2$ + H$_2$O)*** |
| P | 17 (AgNO$_3$) | Al$_2$O$_3$ | 1.0 (CsCl) |
| Q | 17 (AgNO$_3$) | Al$_2$O$_3$ | 0.44 (KCl) |
| R | 17 (AgNO$_3$) | Al$_2$O$_3$ | 1.33 (KCl) |
| S | 17 (AgNO$_3$) | Al$_2$O$_3$ | 1.42 (RbCl) |
| T | 17 (AgNO$_3$) | Al$_2$O$_3$ | 0.36 (RbCl) |
| U | 17 (AgNO$_3$) | Al$_2$O$_3$ | 3.1 (Ba(NO$_3$)$_2$) |
| V | 17 (AgNO$_3$) | Al$_2$O$_3$ | 1.45 (BaCl$_2$) |
| W | 17 (AgNO$_3$) | Al$_2$O$_3$ | 0.24 (Br$_2$)** |
| X | 17 (AgNO$_3$) | Al$_2$O$_3$ | 1.76 (RbNO$_3$) |
| Y | 18.9 (AgNO$_3$) | Al$_2$O$_3$ | 1.0 (CsCl) |
| Z | 18.9 (AgNO$_3$) | Al$_2$O$_3$ | 1.26 (CsBr) |
| AA | 18.9 (AgNO$_3$) | Al$_2$O$_3$ | 1.16 (CsNO$_3$) |
| BB | 19 (Ag$_2$C$_2$O$_4$) | Al$_2$O$_3$ | 0 |

*milligram of promoter (based on weight of promoter compound) per gram of silver-treated support.
**prepared by dissolving elemental Br$_2$ in carbon tetrachloride (CCl$_4$), then the Br$_2$—CCl$_4$ solution was added to support which had previously been treated with silver and promoter (if employed); after mixing, then soaking for about 30 minutes, the CCl$_4$ was removed by evaporation on a rotary evaporator, and finally catalyst was calcined and reduced as described above.
*As in  above, Br$_2$ was dissolved in CCl$_4$, then enough water added to produce a two-phase system, which was then added to the previously Ag- and Cs-treated support; after soaking for about 30 minutes, catalyst was dried, calcined and reduced as described above.
[1] 3/16" pellets with a surface area of 0.26 m$^2$/g, a total pore volume of 0.23 cc(Hg)/gm, median pore diameter of 19$\mu$, a packing density of 0.90 g/cm$^3$, and a chemical composition (wt %) as follows: alumina - 84.7, SiO$_2$ - 13.4, Fe$_2$O$_3$ - 0.21, TiO$_2$ - 0.47, CaO - 0.21, MgO - 0.12, Na$_2$O - 0.15, K$_2$O - 0.26.
[2] 3/16" spheres with a surface area of 0.39 m$^2$/g, a total pore volume of 0.36 cc(Hg)/gm, median pore diameter of 5.4$\mu$, a packing density of 0.94 g/cm$^3$ and a chemical composition (wt %) as follows: Al$_2$O$_3$ - 86.1, SiO$_2$ - 11.8, Fe$_2$O$_3$ - 0.2, TiO$_2$ - 0.1, CaO - 0.4, MgO - 0.4, Na$_2$O - 0.4, K$_2$O - 0.6.
[3] ¼" rings having a surface area of 0.43 m$^2$/g, a total pore volume of 0.37 cc(Hg)/gm, a median pore diameter of 7$\mu$, a packing density of 0.80 g/cm$^3$, and a chemical composition (wt %) as follows: Al$_2$O$_3$ - 93.1, SiO$_2$ - 5.6, Fe$_2$O$_3$ - 0.3, TiO$_2$ - 0.1, CaO - 0.1, MgO - 0.3, Na$_2$O - 0.1, K$_2$O - 0.1.
[4] 3/16" spheres having a surface area of 0.13 m$^2$/g, a total pore volume of 0.37 cc(Hg)/gm, a median pore diameter of 32.5$\mu$, a packing density of 0.88 g/cm$^3$, and a chemical composition (wt %) as follows: Al$_2$O$_3$ - 85.0, SiO$_2$ - 12.0, and the remaining 3% as Fe$_2$O$_3$, TiO$_2$, CaO, MgO, Na$_2$O and K$_2$O.

Silver was deposited on other supports as well, following the same general procedure as above. Thus, 8.0% Ag on ZnO was prepared by dissolving 0.26 g of AgNO$_3$ in 10 mL of distilled water, then adding to the solution 2 g of uncalcined ZnO (having a surface area of 3.9 m$^2$/g, and a particle diameter in the range of about 75-150$\mu$). This material was then dried as described above and is designated as Catalyst CC.

Titania supported catalyst was prepared by calcining TiO$_2$ (having a surface area of about 0.5 m$^2$/g, a particle diameter in the range of about 40-75$\mu$) in oxygen at 450° for about 4 hours. Three grams of this treated TiO$_2$ was then slurried in about 10 mL of distilled water, to which was added a solution of about 10 mL of distilled water containing 73 mg of AgNO$_3$. The combination was thoroughly mixed, then dried as described above. The resulting catalyst, containing about 1.9% Ag, is designated as Catalyst DD.

A higher silver loading-titania supported catalyst was prepared by slurrying 3 g of TiO$_2$ was calcined as described above in 150 mL of distilled water, then slowly adding to the slurry a solution of 0.26 g of AgNO$_3$ in about 10 mL of distilled water. The mixture was heated for about 1 hour to 80°–90° C., then enough formaldehyde was added dropwise until no further silver was precipitated upon addition of HCl to an aliquot of the supernatant liquid. The resulting catalyst had a silver loading of 5.2% and is designated Catalyst EE.

A calcium oxide supported catalyst was prepared by adding 2.0 g of calcined CaO to 10 mL of distilled water in which was dissolved 0.26 g of silver nitrate. The mixture was warmed to ~50° C. for ~1 hour, then water was removed under reduced pressure on a rotary evaporator at a temperature of about 60°–70° C., and the sample then dried by placing in a forced air oven at 120° C. for 1 hour. The resulting catalyst is referred to as Catalyst FF.

A silica-supported catalyst was prepared as per the general procedure set forth above using a silica support having a surface area of 0.18 m$^2$/g, and a particle diameter in the range of 75–250μ. The resulting catalyst had a silver loading of 5 wt % and is designated as Catalyst GG.

A barium oxide supported catalyst was prepared as per the general procedure set forth above using a barium oxide support having a support area of about 1 m$^2$/g, and a particle diameter in the range of about 40–75μ. The resulting catalyst had a silver loading of 6.3 wt % and is designated as Catalyst HH.

Boron nitride (BN; Catalyst II), silicon nitride (Si$_3$N$_4$; Catalyst JJ) and silicon carbide (SiC; Catalyst KK) supported catalysts were prepared in accordance with the standard procedure set forth above. In each case, support was contacted with the necessary amount of aqueous silver nitrate to achieve a 5 wt % Ag on support catalyst. After soaking for about 30 minutes, water was removed on a rotary evaporator, catalyst dried in air at 120° C., then catalyst loaded into a reactor for in situ activation, which consisted of calcination for 4 hrs. at 350° C. in a stream of 20% O$_2$/80% He, followed by reduction for 1 hr. at 350° C. in a stream of 20% H$_2$/80% He. The catalyst designations, supports used and support properties are summarized below.

| Support (surface area) | Resulting 5 wt % Ag catalyst |
|---|---|
| BN (2.9) | II |
| Si$_3$N$_4$ (11.9) | JJ |
| SiC (0.12) | KK |

EXAMPLE 2

Effect of Silver Loading Level

In all of the following catalyst evaluation runs, catalysts were evaluated under steady state conditions in a 1 atmosphere flow reactor system.

All catalysts were evaluated at steady-state conditions using a one atm, single-pass flow reactor. The reactor tube was constructed of pyrex and the catalyst charge (between 0.1 and 20.0 g) was held in place by means of a pyrex frit. The geometries of the reactor and catalyst particles as well as bed depth were chosen to maintain and measure the true kinetic and catalytic aspects of the reaction. A chromel/alumel thermocouple sheathed in stainless steel was embedded within the catalyst bed to measure the true reaction temperature.

The feed gases C$_4$H$_6$ and O$_2$, as well as the diluent He, were added using mass flow controllers, which permitted highly accurate and reproducible flow rates of C$_4$H$_6$, O$_2$, and He regardless of pressure changes from the supply cylinders or the reactor system downstream from the controllers.

Reaction product analyses (as well as feed composition analyses) were made using an in-line gas sampling loop connected directly to the inlet of a Varian 3760 gas chromotograph. Both thermal conductivity (TC) and flame ionization (FI) detectors [(connected in series below the packed Chromosorb 101 column (8 ft. by 2 mm id pyrex capillary column)] were used to analyze all of the reaction products. The TC detector gave quantitative analyses for O$_2$, CO$_2$, H$_2$O, and HCHO (if present), while the FI detector was used for organic molecules such as C$_4$H$_6$, butadiene monoxide, crotonaldehyde, 2,5-dihydrofuran, furan and acrolein. In practice, however, usually only the selective epoxidation product and olefin feedstock were present as organic molecules. Further, by means of a switching valve, it was possible to divert the feed stream through the in-line sample loop prior to passage over the catalyst. In this way, quantitative analysis of the feed stream and comparison to the corresponding data from the reactor effluent were possible, thereby providing very accurate measurements of both conversion levels and product selectivities. Output from both the TC and FI detectors were integrated using computing integrators which were programmed to give both absolute quantities and rates of formation. All reactor exit lines were heated and maintained at 125°–140° C. to prevent product condensation.

The GC analysis was performed using the following temperature programming schedule: an initial temperature of 100° C. was held for 5 minutes, followed by a temperature program rate of +10° C./min up to a final temperature of 200° C. which was then held for 7 minutes. The helium GC carrier rate was 20 mL/min.

In this example, the effect of silver loading level on feed olefin conversion and product selectivity was investigated. Reaction parameters and results are presented in Table 2.

TABLE 2

| | Reaction Parameters | | | | |
|---|---|---|---|---|---|
| Catalyst | Temp, °C. | Gas Feed** (He/O$_2$/C$_4$H$_6$) | Total Gas Flow (in mL (STP)/min) | C$_4$H$_6$ Conversion, % | Product Selectivity, % |
| Ag powder | 225 | 0:1:1 | 17.6 | 0.25 | 70 |
| Ag$_2$O* | 225 | 0:1:1 | 17.6 | 0.01 | 60 |
| A (1.1% Ag on Al$_2$O$_3$) | 250 | 0:1:1 | 20 | 0.8 | 68 |
| A' (5% Ag on Al$_2$O$_3$) | 250 | 0:1:1 | 20 | 1.5 | 74 |
| B (15% Ag on Al$_2$O$_3$) | 250 | 0:1:1 | 18 | 2.4 | 67 |
| B' (15% Ag on Al$_2$O$_3$) | 250 | 0:1:1 | 18.6 | 1.4 | 68 |
| B" (15% Ag on Al$_2$O$_3$) | 250 | 0:1:1 | 16.6 | 1.8 | 71 |
| C (17% Ag on Al$_2$O$_3$) | 250 | 0:1:1 | 18.5 | 2.6 | 75 |
| C (17% Ag on Al$_2$O$_3$) | 225 | 0:1:1 | 18.5 | 1.1 | 88 |
| D (19% Ag on Al$_2$O$_3$) | 250 | 0:1:1 | 17.4 | 2.5 | 81 |

TABLE 2-continued

| Catalyst | Reaction Parameters | | | C$_4$H$_6$ Conversion, % | Product Selectivity, % |
|---|---|---|---|---|---|
| | Temp, °C. | Gas Feed** (He/O$_2$/C$_4$H$_6$) | Total Gas Flow (in mL (STP)/min) | | |
| E (38% Ag on Al$_2$O$_3$) | 250 | 0:1:1 | 18.8 | 2.7 | 89 |

*Grade 1 Ag$_2$O powder was used as obtained from the supplier, activated by heating at 350° C. in flowing hydrogen. The temperature was maintained at about 350° C. by initially introducing 5% H$_2$ in He, with the hydrogen content gradually increased to about 20% (remainder He), and conditions of 20% H$_2$/80% He and 350° C. maintained for one hour before reactant feed commenced.
**Volumetric ratio The above results demonstrate that high catalyst activity and selectivity are obtained with both unsupported silver, and supported silver catalysts over a wide range of loading levels. As one might expect, higher activities are obtained at higher silver loading levels. It is of note that selectivity is not adversely affected even at increasing butadiene conversion levels.

EXAMPLE 3

Effect of Adding Promoters

A series of catalyst evaluations were carried out employing the same experimental setup described in Example 2. A variety of promoted catalysts were tested, with reaction parameters and results set forth in Table 3.

TABLE 3

| Catalyst | Reaction Parameters | | | C$_4$H$_6$ Conversion, % | Product Selectivity, % |
|---|---|---|---|---|---|
| | Temp, °C. | Gas Feed (He/O$_2$/C$_4$H$_6$) | Total Gas Flow in mL (STP)/min | | |
| A (1.1% Ag/Al$_2$O$_3$) | 250 | 0:1:1 | 20 | 0.8 | 68 |
| A + 1.0 mg (CsCl per g. catalyst | 250 | 0:1:1 | 20 | 10.0 | 96 |
| F ((CsCl)—5% Ag/Al$_2$O$_3$) | 225 | 0:1:1 | 20 | 4.5 | 94 |
| | 250 | 0:1:1 | 20 | 9.5 | 88 |
| B' (15% Ag/Al$_2$O$_3$ spheres) | 225 | 0:1:1 | 21.0 | 0.5 | 87 |
| | 250 | 0:1:1 | 18.6 | 1.4 | 68 |
| H ((CsCl)—15% Ag/Al$_2$O$_3$) | 225 | 0:1:1 | 20 | 15 | 93 |
| | 250 | 0:1:1 | 20 | 23 | 89 |
| G ((CsCl)—15% Ag/Al$_2$O$_3$) | 225 | 0:1:1 | 20 | 9.4 | 94 |
| I ((CsCl)—15% Ag/Al$_2$O$_3$) | 225 | 0:1:1 | 18.2 | 9.8 | 93 |
| | 225 | 0:1:1 | 40.5 | 9.5 | 95 |
| | 225 | 0:1:1 | 82.2 | 9.2 | 95 |
| | 250 | 0:1:1 | 18.2 | 16 | 95 |
| J ((CsCl)—15% Ag/Al$_2$O$_3$) | 225 | 0:1:1 | 16.1 | 7.7 | 93 |
| | 225 | 0:1:1 | 35.5 | 7.3 | 140 |
| | 240 | 0:1:1 | 35.5 | 11.3 | 93 |
| | 250 | 0:1:1 | 16.1 | 11.5 | 90 |
| K ((CsCl & Br$_2$)—15% Ag/Al$_2$O$_3$) | 225 | 0:1:1 | 17.4 | 10 | 94 |
| | 225 | 0:1:1 | 38.0 | 9.9 | 95 |
| | 240 | 0:1:1 | 38.0 | 14 | 93 |
| | 250 | 0:1:1 | 17.4 | 14 | 90 |
| L ((CsCl & Br$_2$)—15% Ag/Al$_2$O$_3$) | 225 | 0:1:1 | 17.1 | 10.5 | 94 |
| | 225 | 0:1:1 | 38.0 | 9.8 | 95 |
| | 250 | 0:1:1 | 17.1 | 16 | 93 |
| M ((CsCl & Br$_2$)—15% Ag/Al$_2$O$_3$) | 225 | 0:1:1 | 17.6 | 8 | 94 |
| | 225 | 0:1:1 | 39.0 | 7.2 | 96 |
| | 240 | 0:1:1 | 39.0 | 11.8 | 94 |
| | 240 | 0:1:1 | 55.0 | 11.1 | 94 |
| | 250 | 0:1:1 | 17.6 | 12 | 91 |
| N ((CsCl & Br$_2$)—15% Ag/Al$_2$O$_3$) | 225 | 0:1:1 | 16.5 | 6.8 | 93 |
| | 225 | 0:1:1 | 36.8 | 6.4 | 95 |
| | 240 | 0:1:1 | 36.8 | 10.3 | 93 |
| | 250 | 0:1:1 | 16.5 | 11.3 | 89 |
| O ((CsCl & Br$_2$)—15% Ag/Al$_2$O$_3$) | 225 | 0:1:1 | 17.2 | 4.4 | 90 |
| | 225 | 0:1:1 | 36.4 | 4.0 | 93 |
| | 240 | 0:1:1 | 36.4 | 7.5 | 90 |
| | 240 | 4:1:1 | 56.6 | 7.3 | 87 |
| | 240 | 0:1:1 | 70.6 | 7.1 | 93 |
| | 240 | 2:1:1 | 72.3 | 7.6 | 90 |
| | 240 | 1:1:1 | 80.0 | 8.3 | 92 |
| | 250 | 0:1:1 | 17.2 | 8 | 85 |
| C (17% Ag/Al$_2$O$_3$) | 225 | 0:1:1 | 18.5 | 1.1 | 88 |
| | 250 | 0:1:1 | 18.5 | 2.6 | 75 |
| P (CsCl—17% Ag/Al$_2$O$_3$) | 225 | 0:1:1 | 18.0 | 5.5 | 97 |
| | 250 | 0:1:1 | 18.0 | 11 | 96 |
| Q (KCl—17% Ag/Al$_2$O$_3$) | 225 | 0:1:1 | 18.9 | 0.2 | 96 |
| | 250 | 0:1:1 | 18.9 | 0.5 | 74 |
| R (KCl—17% Ag/Al$_2$O$_3$) | 225 | 0:1:1 | 18.6 | 0.1 | 98 |
| | 250 | 0:1:1 | 18.6 | 0.4 | 75 |
| S (RbCl—17% Ag/Al$_2$O$_3$) | 225 | 0:1:1 | 18.4 | 2.4 | 95 |
| | 250 | 0:1:1 | 18.4 | 5.5 | 89 |
| T (RbCl—17% Ag/Al$_2$O$_3$) | 225 | 0:1:1 | 18.7 | 0.1 | 96 |

TABLE 3-continued

| Catalyst | Reaction Parameters | | | $C_4H_6$ Conversion, % | Product Selectivity, % |
|---|---|---|---|---|---|
| | Temp, °C. | Gas Feed $(He/O_2/C_4H_6)$ | Total Gas Flow in mL (STP)/min | | |
| | 250 | 0:1:1 | 18.7 | 0.3 | 67 |
| U $(Ba(NO_3)_2$—17% Ag/$Al_2O_3$) | 225 | 0:1:1 | 18.3 | 0.8 | 90 |
| | 250 | 0:1:1 | 18.3 | 1.7 | 76 |
| V ($BaCl_2$—17% Ag/$Al_2O_3$) | 250 | 0:1:1 | 18.4 | 0.3 | 83 |
| W ($Br_2$—17% Ag/$Al_2O_3$) | 250 | 0:1:1 | 18.2 | 0.2 | 73 |
| X ($RbNO_3$—17% Ag/$Al_2O_3$) | 225 | 0:1:1 | 18.4 | 4.5 | 92 |
| | 250 | 0:1:1 | 18.4 | 9.9 | 86 |
| D (19% Ag on $Al_2O_3$) | 250 | 0:1:1 | 17.4 | 2.5 | 81 |
| Y (CsCl—19% Ag/$Al_2O_3$) | 250 | 0:1:1 | 17.5 | 15.1 | 94 |
| Z (CsBr—19% Ag/$Al_2O_3$) | 250 | 0:1:1 | 18.2 | 5.0 | 96 |
| AA ($CsNO_3$—19% Ag/$Al_2O_3$) | 250 | 0:1:1 | 16.5 | 15 | 77 |

These results demonstrate that alkali metal and alkaline earth metal compounds increase the rate of butadiene monoxide formation and/or increase the selectivity to the desired product (relative to that obtained with unpromoted catalyst), with both rate and selectivity frequently being improved. The addition of halogens is also shown to be an effective means to increase the selectivity to butadiene monoxide.

The benefit of these additives is observed to be independent of the silver loading and the nature of the support employed.

EXAMPLE 4

Effect of Various Catalyst Supports

A series of catalyst evaluations were carried out employing the same experimental setup described in Example 2. A variety of supported catalysts, prepared using different catalyst supports, were tested. The reaction parameters and results are set forth in Table 4.

TABLE 4

| Catalyst | Reaction Parameters | | | $C_4H_6$ Conversion, % | Product Selectivity, % |
|---|---|---|---|---|---|
| | Temp, °C. | Gas Feed $(He/O_2/C_4H_6)$ | Total Gas Flow in mL (STP)/min | | |
| A' (5% Ag/$Al_2O_3$) | 250 | 0:1:1 | 20 | 1.5 | 74 |
| CC (8.0% Ag/ZnO) | 250 | 0:1:1 | 19.7 | 0.2 | 70 |
| DD (1.9% Ag/$TiO_2$) | 225 | 0:1:1 | 20 | 0.06 | 60 |
| EE (5.2% Ag/$TiO_2$) | 225 | 0:1:1 | 18.3 | 0.03 | 53 |
| FF (5% Ag/CaO) | 250 | 0:1:1 | 19.0 | 0.2 | 47 |
| GG (5% Ag/$SiO_2$) | 250 | 0:1:1 | 20 | 1.1 | 87 |
| HH (6.3% Ag/BaO) | 250 | 0:1:1 | 20 | 0.1 | 87 |
| II (5% Ag/BN) | 200 | 0:1:1 | 20 | 0.2 | 68 |
| | 225 | 0:1:1 | 20 | 0.8 | 61 |
| JJ (5% Ag/$Si_3N_4$) | 225 | 0:1:1 | 20 | 0.1 | 66 |
| | 275 | 0:1:1 | 20 | 0.9 | 38 |
| KK (5% Ag/SiC) | 225 | 0:1:1 | 20 | 0.1 | 70 |
| | 275 | 0:1:1 | 20 | 0.9 | 61 |

These results demonstrate that a variety of supports are effective for the highly selective conversion of butadiene to butadiene monoxide. The results also indicate that alumina is the presently preferred support for use in the practice of the present invention.

EXAMPLE 5

Selective Epoxidation of a Variety of Olefins

The same experimental set-up described in Example 2 was employed with t-butylethylene as the olefin feed and 1.77 g of Catalyst P (see Table 1). Reaction parameters and results are set forth in Table 5.

TABLE 5 t-Butylethylene (TBE) Oxidation

| Reaction Temp., °C. | Gas Feed $(He/TBE/O_2)$ | Total Gas Flow in mL (STP)/min | TBE Conversion, % | Product* Selectivity, % |
|---|---|---|---|---|
| 250 | 25/1/25 | 10 | 0.6 | 41 |
| 250 | 20/1/20 | 10 | 0.2 | >95 |
| 250 | 85/1/85 | 6 | 1.0 | >95 |
| 250 | 200/1/200 | 6 | 1.5 | >95 |
| 275 | 60/1/60 | 6 | 1.9 | 43 |
| 275 | 25/1/25 | 6 | 1.1 | 34 |

*Desired product is t-butylethylene monoxide.

These results demonstrate that olefins having no allylic hydrogens, e.g., t-butyl ethylene, can be selectively oxidized to the mono-epoxide derivative according to the practice of the present invention.

EXAMPLE 6

Comparative Oxidation Reactions

We attempted to repeat the oxidation of olefins higher than ethylene (such as propylene, 1-butene, 2-butene, etc.) as suggested by Brengle & Steward in U.S. No. 2,709,173. In efforts to follow the teachings of the reference, catalyst composition (5% Ag/Al$_2$O$_3$) and reaction parameters as set forth in the reference were followed as closely as possible.

The reaction parameters employed and results obtained are set forth in Table 6.

TABLE 6

| | | Reaction Parameters | | | | Product Selectivity, | |
|---|---|---|---|---|---|---|---|
| | | Temp. | Gas Feed | Total Gas Flow in mL, | Feed Conversion, | | |
| Catalyst | Feed | °C. | (He/O$_2$/olefin | (STP)/min. | % | CO$_2$ | Epoxide |
| A' | Ethylene | 250 | 3:1:1 | 25 | 12 | 53 | 47 |
| A' | Propylene | 250 | 3:1:1 | 24 | 7 | 92 | 0 |
| A' | 1-Butene | 250 | 3:1:1 | 23 | 3 | 92 | 0 |
| A' | 2-Butene | 250 | 3:1:1 | 52.2 | 2 | 98 | 0 |

These results confirm the suggestions of the literature, e.g., "Oxidation of butadiene with Ag$_2$O at 551° K. (278° C.) by means of pulse technique gave only CO$_2$ and a small amount of acrylaldehyde." [Bull. Chem. Soc., Jap. 51, 3061-3062 (1978)], and "Silver and silver oxide catalysts, although suitable for the oxidation of ethylene to ethylene oxide, do not seem to be similarly effective for the oxidation of the four-carbon olefins." [Ind. and Eng. Chem., 44, 594-603 (1952)]. The data set forth in Table 6 demonstrate that propylene, 1-butene and 2-butene are converted almost exclusively to CO$_2$, with no observable epoxide formation.

These data refute the suggestion by Brengle and Stewart that the "lower molecular weight hydrocarbon olefins in particular are adaptable to this invention [preparation of olefin oxides]. Those which are normally gaseous, such as ethylene, propene, butene-1, butene-2 and butadiene, for example, are more suitable, with ethylene being preferred." [See Col. 2, l. 64-68]. The data set forth above confirm the suggestions of the art, i.e., that silver catalyzed oxidation is effective only for the production of epoxide from ethylene.

The more recent disclosures of Rao in U.S. No. 4,429,055 and U.S. No. 4,474,977 are consistent with the suggestions of the above-cited prior art. Rao determined that among the lower olefins, only ethylene can be selectively directly epoxidized. When Rao carried out the oxidation of propylene, 1-butene and 1,3-butadiene under epoxidation conditions, no epoxide product was observed. For example, propylene conversion was calculated to be 46.1% based on the content of oxygen in the feed, with the primary product formed being acrolein (28.8% selectivity). The only other products of propylene oxidation were CO$_2$ and H$_2$O.

Similarly, when Rao evaluated the oxidation of 1,3-butadiene, the observed products were furan, acrolein, dihydrofuran and trihydrofuran:

The selectivity to furan is 22.4% and to acrolein is 5.1%. Gas chromatographic analysis shows two other peaks besides furan and acrolein. They have retention times the same as a mixture of dihydrofuran and trihydrofuran.

See Col. 4, lines 1-5 of '997, Thus, Rao, consistently with all other relevant prior art, neither discloses nor suggests the selective formation of mono-epoxides from olefins such as butadiene, i.e., olefins having no allylic hydrogens.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

We claim:

1. A process for the selective monoepoxidation of olefins having the structure:

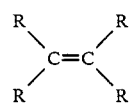

wherein each R is independently selected from the group consisting of:
(a) hydrogen,
(b) aryl and substituted aryl groups having in the range of 7 up to 20 carbon atoms,
(c) tertiary alkyl groups of the formula:

where each R' is independently:
R",

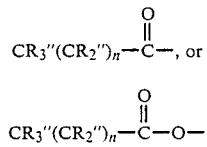

where R" is H, C$_1$-C$_{10}$ alkyl or substituted alkyl, an aryl or substituted aryl grup having 6 up to 20 carbon atoms, and n is a whole number from 0-12;
(d)

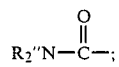

(e) R$_2$"N—;
(f) CR$_2$"=CR"—(CR"=CR")$_y$, where y is an integer from 0-20; and
(g)

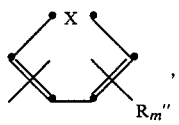

where X is O,
and m is an integer from 0-3,
with the proviso that said olefin have no allylic hydrogens and that at least one R-group not be hydrogen;
said process comprising contacting said olefin with a sufficient quantity of an oxygen-containing gas so as to maintain the molar ratio of olefin to oxygen in the range of 0.01 up to 20, in the presence of a promoted silver-containing catalyst containing at least one promoter selected from the group consisting of:
the salts of alkali metals,
the oxides of alkali metals,
the salts of alkaline earth metals,
the oxides of alkaline earth metals,
organic halides,
inorganic halides,
acid halides, and
elemental halogens,
as well as mixtures of any two or more thereof at a pressure in the range of 0.1 up to 100 atmospheres, at a temperature in the range of 75 up to 325° C. for a time sufficient to obtain olefin conversions in the range of 0.5 up to 75%.

2. A process in accordance with claim 1 wherein said silver catalyst is a supported silver catalyst comprising in the range of 0.5 up to 75 weight % elemental silver.

3. A process in accordance with claim 2 wherein said supported silver catalyst is supported on an inorganic support having a surface area no greater than about 50 m$^2$/g.

4. A process in accordance with claim 3 wherein said inorganic support is selected from the group consisting of
silica,
alumina,
silica-alumina,
zeolites,
titanium oxide,
lanthanum oxide,
magnesium oxide,
boron nitride,
boron carbide,
silicon nitride,
silicon carbide,
zinc oxide,
tin oxide,
iron oxide,
calcium oxide,
barium oxide,
strontium oxide,
zirconium oxide,
carbon,
boron phosphate,
zirconium phosphate,
and mixtures of any two or more thereof.

5. A process in accordance with claim 2 wherein said silver catalyst comprises in the range of 0.001 up to 10 weight %, based on the total weight of catalyst, including support, of at least one promoter selected from the group consisting of:
the salts of alkali metals,
the oxides of alkali metals,
the salts of alkaline earth metals,
the oxides of alkaline earth metals,
organic halides,
inorganic halides,
acid halides, and
elemental halogens,
as well as mixtures of any two or more thereof.

6. A process in accordance with claim 5 wherein said promoter is a halide salt of an alkali metal.

7. A process in accordance with claim 1 wherein said olefin is selected from the group consisting of:
butadiene,
tertiarybutyl ethylene,
vinyl furan,
methyl vinyl ketone, and
methyl acrylate,
as well as mixtures of any two or more thereof.

8. A process in accordance with claim 7 wherein said silver catalyst comprises:
in the range of about 1 up to 30 weight % silver,
in the range of about 0.001 up to 10 weight percent of an alkali metal halide, and
an alumina support having a surface area of less than about 10 m$^2$/g;
wherein said weight percentages are based on the total weight of catalyst.

9. A process in accordance with claim 7 wherein said silver catalyst comprises:
in the range of about 2 up to 20 weight percent silver,
in the range of 0.01 up to 2 weight percent of an alkali metal halide,
an alumina support having a surface area of less than about 1 m$^2$/g;
wherein said weight percentages are based on the total weight of catalyst.

10. A process in accordance with claim 9 wherein said alkali metal halide is selected from the group consisting of cesium chloride and cesium bromide.

11. A process in accordance with claim 8 wherein said contacting is carried out at a temperature in the range of about 175° up to 250° C., at a pressure in the range of about 1 up to 30 atmospheres for a time sufficient to obtain olefin conversions in the range of about 5 up to 30%.

12. A process in accordance with claim 9 wherein said contacting is carried out at a temperature in the range of about 175° up to 250° C., at a pressure in the range of abut 1 up to 30 atmospheres for a time sufficient to obtain olefin conversions in the range of about 5 up to 30%.

13. A process in accordance with claim 1 wherein said oxygen-containing gas is selected from the group consisting of:
air,
inert gas diluted air,
inert gas diluted oxygen,
oxygen-enriched air, and
substantially purified oxygen.

14. A process in accordance with claim 1 wherein said olefin is butadiene.

* * * * *